US011614622B2

United States Patent
Mair et al.

(10) Patent No.: US 11,614,622 B2
(45) Date of Patent: Mar. 28, 2023

(54) HEAD-MOUNTED DISPLAY SYSTEM AND METHOD FOR CONTROLLING A MEDICAL IMAGING DEVICE

(71) Applicant: BHS Technologies GmbH, Innsbruck (AT)

(72) Inventors: Michael Mair, Rum (AT); Bernhard Höckner, Innsbruck (AT); Luis Fernando Ayuso Perez, Innsbruck (AT); Gregor Burger, Völs (AT)

(73) Assignee: BHS Technologies GmbH, Innsbruck (AT)

(*) Notice: Subject to any disclaimer, the term of this patent is extended or adjusted under 35 U.S.C. 154(b) by 0 days.

(21) Appl. No.: 17/145,429

(22) Filed: Jan. 11, 2021

(65) Prior Publication Data
US 2021/0215932 A1    Jul. 15, 2021

(30) Foreign Application Priority Data
Jan. 9, 2020   (EP) .................................. 20151040

(51) Int. Cl.
*G02B 27/01* (2006.01)
*A61B 34/00* (2016.01)
(Continued)

(52) U.S. Cl.
CPC ............ *G02B 27/017* (2013.01); *A61B 34/25* (2016.02); *A61B 34/30* (2016.02); *A61B 90/20* (2016.02);
(Continued)

(58) Field of Classification Search
None
See application file for complete search history.

(56) References Cited

U.S. PATENT DOCUMENTS

| 4,989,253 A | 1/1991 | Liang et al. |
| 5,345,087 A | 9/1994 | Luber et al. |
| (Continued) | | |

FOREIGN PATENT DOCUMENTS

| AT | 519845 | 10/2018 |
| DE | 4202505 | 8/1993 |
| (Continued) | | |

OTHER PUBLICATIONS

Superimpose—definition downloaded on Jun. 22, 2022 from https://www.macmillandictionary/american/superimpose 5 pages (Year: 2022).*
(Continued)

*Primary Examiner* — Dorothy Harris

(57) ABSTRACT

The present invention relates to a head-mounted display system (1) for controlling a medical imaging device (20), comprising: a head-mounted display (10) to be worn by an operator, comprising a display (12) configured to display a medical image with a predetermined center of view (121) and a command menu (122) providing at least a first set of commands (123) as distinct first command fields, a tracking system (14) to track a movement representative of the operator's eye (30) and/or head movement, wherein a command of the at least first set of commands (122a) of the command menu (122) is selectable based on the tracked eye and/or head movement, and a control device (40) configured to receive a selected command and to control the medical imaging device (20) accordingly.

21 Claims, 2 Drawing Sheets

(51) Int. Cl.
*A61B 34/30* (2016.01)
*A61B 90/20* (2016.01)
*G02B 27/00* (2006.01)
*G06F 3/01* (2006.01)
*G06F 3/0482* (2013.01)

(52) U.S. Cl.
CPC .... *G02B 27/0093* (2013.01); *A61B 2034/301* (2016.02); *G06F 3/011* (2013.01); *G06F 3/012* (2013.01); *G06F 3/013* (2013.01); *G06F 3/0482* (2013.01)

(56) References Cited

U.S. PATENT DOCUMENTS

| | | | |
|---|---|---|---|
| 6,847,336 | B1 | 1/2005 | Lemelson et al. |
| 7,851,736 | B2 | 12/2010 | Spahn |
| 9,020,613 | B2 | 4/2015 | Taylor et al. |
| 10,188,552 | B2 | 1/2019 | He et al. |
| 10,314,665 | B2 | 6/2019 | Bismuth et al. |
| 2006/0119539 | A1 | 6/2006 | Kato et al. |
| 2008/0141181 | A1* | 6/2008 | Ishigaki ............. G06F 3/04847 715/863 |
| 2008/0180521 | A1 | 7/2008 | Ahearn |
| 2009/0158167 | A1* | 6/2009 | Wang ............. G06F 3/0482 715/745 |
| 2010/0049046 | A1* | 2/2010 | Peiffer ............. A61B 8/13 600/443 |
| 2014/0035811 | A1* | 2/2014 | Guehring ............. G09G 5/006 345/156 |
| 2015/0219901 | A1 | 8/2015 | Morimoto |
| 2016/0161746 | A1 | 6/2016 | Ahearn |
| 2016/0225192 | A1 | 8/2016 | Jones et al. |
| 2017/0196453 | A1 | 7/2017 | Papac |
| 2018/0049811 | A1 | 2/2018 | Themelis |
| 2018/0110571 | A1* | 4/2018 | Hallen ............. A61B 34/37 |
| 2019/0053700 | A1 | 2/2019 | Tesar |
| 2019/0380792 | A1* | 12/2019 | Poltaretskyi ........... A61B 90/06 |
| 2019/0391642 | A1 | 12/2019 | Eil |
| 2020/0333578 | A1 | 10/2020 | Capeli et al. |
| 2021/0278904 | A1* | 9/2021 | Ma ............. G06F 3/04812 |

FOREIGN PATENT DOCUMENTS

| | | |
|---|---|---|
| DE | 102006001505 | 7/2007 |
| EP | 3540580 | 9/2019 |
| ES | 1068414 | 10/2008 |
| JP | 2014-068184 | 4/2014 |
| WO | WO 95/11473 | 4/1995 |
| WO | WO 02/086590 | 10/2002 |
| WO | WO 2018/170522 | 9/2018 |

OTHER PUBLICATIONS

Xu et al. "RingText: Dwell-Free and Hands-Free Text Entry for Mobile Head-Mounted Displays using Head Motions", IEEE Transactions on Visualization and Computer Graphics, 25(5): 1991-2001, May 2019.

* cited by examiner

HEAD-MOUNTED DISPLAY SYSTEM AND METHOD FOR CONTROLLING A MEDICAL IMAGING DEVICE

RELATED APPLICATION

This application claims the benefit of priority of European Patent Application No. 20151040.1 filed on Jan. 9, 2020, the contents of which are incorporated herein by reference in their entirety.

FIELD AND BACKGROUND OF THE INVENTION

The invention relates to a head-mounted display system for controlling a medical imaging device, a method for controlling a medical imaging device and a computer program product to execute the method.

Medical imaging devices are often used to support a surgeon during surgery by providing insight or enlarged images of the operating field and/or to record relevant images. However, the center of view, the viewing angle, the magnification or other settings of the medical imaging device may have to be adapted during the course of a surgical procedure. Such manual adaptions require an operator's intervention, which may result in disturbances in terms of sterility, coordination of operations or distractions of the surgeon.

Different approaches have been proposed to minimize the disturbances caused by manual adaptions of the medical imaging device. For example, U.S. Pat. No. 4,989,253 A discloses a microscope with a voice activated control system which permits precise location of the microscope and precise focusing by means of voice commands uttered by the microscope operator. Although manual interventions can be avoided, problems arise in the accurate determination of the respective movement path by the surgeon and due to the requirement of the use of predetermined vocabulary. In particular, voice commands may be unintendedly initiated during communication between the surgical personal.

Alternatively, DE 42 02 505 B4 proposes a contactless guidance system for the spatial positioning of a surgical microscope by directly moving the surgical microscope in accordance with a head movement of the operator. However, such system allows only adaptions of the surgical microscope directly corresponding to the operator's head movement. Furthermore, an unintended or false movement of the operator's head may result in a consequent movement of the surgical microscope with severe consequences.

SUMMARY OF THE INVENTION

Accordingly, it is an object of the present invention to provide a control of a medical imaging device in a contactless manner with enhanced control options while minimizing the risk of initiating an unintended command.

The object is solved by a head-mounted display system for controlling a medical imaging device according to claim 1, a method for controlling a medical imaging device according to claim 16, and a computer program product according to claim 18. Further aspects of the present invention are subject of the dependent claims.

According to one aspect, a head-mounted display system for controlling a medical imaging device comprises: a head-mounted display to be worn by an operator, comprising a display configured to display a medical image with a predetermined center of view and a command menu providing at least a first set of commands as distinct first command fields, a tracking system to track a movement representative of the operator's eye and/or head movement, wherein a command of the at least first set of commands of the command menu is selectable based on the tracked eye and/or head movement, and a control device configured to receive a selected command and to control the medical imaging device accordingly.

The medical image displayed in the display of the head-mounted display corresponds to the image received by the medical imaging device or at least a section thereof. The predetermined center of view may be predetermined geometrically, e.g. as the center of the image displayed in the display, or based on the current viewing angle of the operator wearing the head-mounted display. The viewing angle may be derived from a tracked eye movement or assumed by the position of the head-mounted display in consideration of a viewing angle perpendicular or with another predetermined viewing angle to the display corresponding to a usual operator's orientation. Alternatively or in addition, the center of view may be determined under consideration of the operating field or a specific part thereof, e.g. based on a marker. If the operating field or a specific part thereof is considered for the determination of the predetermined center of view in addition to other aspects, the predetermined center of view may, for example, be defined according to the operator's viewing angle as long as the viewing angle does not result in a center of view exceeding a predetermined distance from the operating field or a specific part thereof.

Next to the medical image, the display of the head-mounted display displays a command menu providing at least a first set of commands as distinct first command fields. The command menu may be superimposed over the medical image or displayed in a separate section of the display. In the event of a separate display section for the command menu or at least parts thereof, the medical image is not hidden by obscuring command fields. However, a superimposition of the command menu or at least parts thereof may be advantageous to save display space for the medical image and/or reduce the distance to the predetermined center of view to select commands as described later. In such event, the command menu or at least parts thereof are arranged outside the predetermined center of view to minimize the disturbance of the operator when displayed. In one embodiment, the head-mounted display system may be configured to switch between two modes, the superimposition mode and a separate display section mode.

The command menu providing at least a first set of commands as distinct command fields may comprise command fields to control a movement of the medical imaging device, medical imaging settings like magnification, brightness and/or contrast, and/or recording functions. Accordingly, the head-mounted display system is not only capable of allowing the control of a movement of the medical imaging device to change the center of view and/or the viewing angle but also settings which do not naturally correspond to the movement of the operator's eye or head.

The tracking system to track a movement representative of the operator's eye and/or head movement may be incorporated in the head-mounted display. Such tracking system may comprise a GPS-based tracker, an acceleration sensor or an optical or electromagnetic tracker with regards to a head movement. For example, an optical tracker may comprise two cameras attached to the head-mounted display tracking the head movement with reference to a defined reference point in the operating room. A movement of the operator's eye may be tracked by a camera. Alternatively or in addition, e.g. for redundancy reasons, a tracking system may be separate from the head-mounted display.

Advantageously, the tracking system is configured to track a movement representative of the operator's eye and/or head movement independent from an optical transmission path that may be interrupted by obstacles. Further, a movement representative of the operator's eye and/or head movement is directed to track any object which movement corresponds to the movement of the operator's eye and/or head. Accordingly, an object which moves in correspondence with the operator's head may not only be the operator's head itself, but also, for example, the heat-mounted display or parts thereof as the display, or other components affixed to the operator's head. In terms of a movement of the operator's eye, such movement may be represented by tracking the movement of one or both eyes of the operator. Therefore, the terms eye and eyes may be used synonymously if there's no requirement to be distinguished.

Tracking the movement representative of head movement provides the advantage of selecting a command of the at least first set of commands of the command menu without the need to move the eyes away from the operating field. Alternatively or in addition, the movement representative of the operator's eye movement may be used to select a command of the at least first set of commands of the command menu. This type of selection may be advantageous if, for example, a head movement is hindered or limited for ergonomic reasons.

The selection of a command of the at least first set of commands of the command menu is based on the tracked movement representative of the operator's eye and/or head movement by converting the direction and amount of the tracked movement in a position on the display. If such position corresponds to one of the distinct first command fields, the respective command is selected. Accordingly, the control device of the head-mounted display system is configured to either receive the selected command directly or indirectly by receiving and converting the tracked movement. Depending on the selected command, the control device controls the medical imaging device in accordance with the selected command. The control by the control device is not restricted to a direct control of the medical imaging device. For example, the control device may be configured to control a robot to move the medical imaging device attached to such robot.

The control device may be incorporated in the head-mounted display or the medical imaging device or may be provided as separate control device, e.g. as a personal computer in communication with the head-mounted display and medical imaging device. Separating the control device from the head-mounted display or the medical imaging device may reduce the weight of the respective components to be worn or moved, respectively.

In one embodiment, the distinct first command fields of said at least first set of commands of the commend menu displayed on the display of the head-mounted display are arranged in substantially equal first distances from the predetermined center of view of the medical image.

Due to the substantially equal first distances from the predetermined center of view, the tracked movement to arrive at one of the distinct first command fields can be limited in comparison to command fields arranged in series in a radial direction from the predetermined center of view. Furthermore, an arrangement of the first command fields in substantially equal first distances from the predetermined center of view may allow an operator's head movement to be tracked while still providing the ability to direct the eyes to the operating field. If the eye movement is tracked, the operating field may be still in the field of view. Accordingly, the control of the medical imaging device may be executed without interrupting the medical procedure as neither the operator's hands nor the view of the operator has to leave the operating field.

The term "substantially equal distances" refers to distances that only deviate from each other by minor tolerances. Such minor tolerances do not affect the aforementioned advantages. The ideal arrangement is a circular arrangement of the distinct first command fields with the predetermined center of view as center of the circle. However, the circular arrangement may also be slightly distorted, i.e. slightly oval, with slightly larger distances in directions of enhanced movement capabilities of the operator's head or eyes. Accordingly, the slightly larger distances correspond to a movement of the operator's head or eyes in a left and right direction regarding the longitudinal or craniocaudal axis of the operator.

In some embodiments, the command menu provides a second set of commands as distinct second command fields displayed on the display of the head-mounted display and preferably arranged in substantially equal second distances from the predetermined center of view of the medical image, wherein the second distances of the distinct second command fields are larger than the first distances of the distinct first command fields.

The second set of command fields may therefore be arranged and/or displayed independently from the first set of command fields. In particular, the distinct second command fields of the second set of commands are arranged in substantially equal second distances from the predetermined center of view of the medical image to provide similar advantages as the arrangement of the distinct first command fields in substantially equal first distances. By arranging the distinct second command fields in substantially equal second distances from the predetermined center of view, wherein the second distances of the distinct second command fields are larger than the first distances of the distinct first command fields, the second set of commands surrounds the first set of commands when displayed. Preferably, the second set of commands is close or adjacent to the first set of commands to provide the ability of shortest distances and therefore movements to be tracked.

According to the disclosure, the control device may be configured to deactivate the distinct first command fields when the tracking system indicates that the tracked movement has passed one of the distinct first command fields in a direction away from the predetermined center of view of the medical image to one of the distinct second command fields.

The deactivation of the distinct first command fields may prevent an unintended selection of one of the distinct first command fields when the tracked movement representative of an operator's head or eye movement strikes back over such field. In other words, the selection of command fields is restricted to one of the distinct second command fields after the tracking system has indicated that the tracked movement has passed one of the distinct first command fields in a direction away from the predetermined center of view of the medical image to one of the distinct second command fields.

Advantageously, the control device is configured to assign commands to the first set of commands and the second set of commands based on a frequency and/or probability of use.

In terms of displaying the first set of commands and second set of commands independently, e.g. displaying the second set of commands only on demand or under certain circumstances, and/or arranging the distinct second command fields in substantially equal second distances from the predetermined center of view larger than the substantially equal first distances, the first set of commands preferably comprises the functions used with higher frequency and/or probability of use. Thus, the majority of movements may be kept at a reduced level of movement regarding the arrangement of the first and second set of commands in different distances. If the second set of commands is only displayed on demand or under certain circumstances, the second set of commands does not obscure the medical image when superimposed.

According to the disclosure, the control device may be configured to adapt the assignment of commands to the first set of commands and the second set of commands based on a changed frequency and/or probability of use.

The adaption of the assignment of commands to the first set of commands and the second set of commands may be entered by an input device. Preferably, the control device is configured to adapt the assignment automatically, e.g. by analyzing selected commands over a predetermined time or after the execution of a predetermined number of selected commands. The analysis may be based on determining the distinct frequency of selected commands or under further consideration of weighting factors.

In some embodiments, the command menu further comprises a confirmation field arranged in the predetermined center of view of the medical image to confirm the selected command field.

As an operator may execute a tracked movement and thereby may select a command field unintendedly, the confirmation field prevents the execution of such command. Here, the control device is configured to only control the medical imaging device according to the selected command if the tracked movement further corresponds to the selection of the confirmation field after a command has been selected. Furthermore, the confirmation field allows the execution of a command on demand, i.e. a command does not have to be executed immediately after its selection but only if the confirmation field is selected. In particular, the command in such configuration is only executed if the tracked movement representative of the operator's head or eye movement arrives at the predetermined center of view. In such event, it has to be assumed that the operator's view can be directed on the predetermined center of view to mitigate the risk of initiating the execution of a command without visual control of the operating field.

Alternatively or in addition, the selected command field may be confirmed if a further movement representative of the operator's eye or head movement is not tracked or does not correspond to another command field within a predetermined time range. Alternatively, the control device is configured to control the medical imaging device according to the command field selected first.

Advantageously, the head-mounted display system further comprises an input device, preferably a footswitch, to be activated as a prerequisite for the selection of one of the command fields and/or for displaying the command menu.

Since the medical imaging device does not have to be continuously controlled, the risk of selecting a command unintendedly is further reduced if such selection is only released if an input device is activated. Advantageously, the tracking system also does not track any movement as long as the input device is not activated to avoid unnecessary data collection. Furthermore, the command menu may only be displayed on demand by activating the input device to prevent the medical image from being obscured by the command menu if superimposed or to show the medical image over the full display area without reserving space for a separate display section.

Using a footswitch as input device provides the option of an activation without affecting the sterility. Alternatively, the input device may be any other kind of switch that may be operated by a member of the surgical team under consideration of sterile aspects and authorization.

According to the disclosure, the input device may be configured to be only activated as long as a continuous activation action is applied.

For example, a command may only be selected as long as a footswitch as input device is pressed down. If an activation action is withdrawn or falls under a predetermined level, the ability of selecting a command is deactivated and the command menu may be no further displayed. Furthermore, the control device may be configured to reset the display settings after the no further activation action is applied, i.e. the display settings for the command menu are returned to a default state. Alternatively, the last display settings may be stored and the command menu is displayed with those settings with the next activation of the input device.

In some embodiments, the head-mounted display system further comprises a monitoring device configured to monitor the position of the display and to release the selection of one of the command fields and/or to display the command menu only in positions of the display representing a use of the display by the operator.

Such monitoring device may be incorporated in the head-mounted display. For example, the display of the head-mounted display may be movably supported by a hinge equipped with a sensor to detect the operating state of the display, i.e. a flipped-down position of the display. Alternatively, the spatial position of the display may be detected and compared to the operator's head position. In a variant, the spatial position of the display may be detected and compared to common or uncommon positions of operation, respectively, e.g. an orientation of the display towards the ceiling of an operating room may be assumed as uncommon position so that the selection of commands is not released. In a further variant, the monitoring device comprises a contact switch which is only activated if the head-mounted display is at least worn by the operator. Even though the different monitoring options are described as alternatives, combinations are possible to enhance the safety in terms of redundancy or consideration of multiple prerequisites.

Advantageously, the head-mounted display system further provides different operating states and is configured to release the selection of one of the command fields and/or display the command menu only in predetermined operating states.

The different operating states may be states representing non-surgical operations like commissioning, maintenance, training, preparation and the like. Those operating states may require less safety measures as no surgery is performed. However, in the event of a surgery, different operating states with different levels of safety may be available. In severe situations, the medical imaging device may not be allowed to move and/or the medical image should be displayed without showing any disturbing command fields. Accordingly, any command field representative of moving the medical device are not released and/or the command menu or at least parts thereof are not displayed.

According to the disclosure, the tracking system may be configured to track the movement representative of the eye movement to control the center of view of the medical image on the display and to track the movement representative of the head movement to select one of the command fields.

The movement representative of the eye movement controls the predetermined center of view of the medical image on the display to correspond to the viewing angle in a predetermined relationship, preferably to be coincident with the center of view of the operator. Accordingly, the center of view of the medical image follows the eye movement without the requirement of the selection of a command field. However, such tracking may be released on demand by a prior selection of a respective command field based on a tracked head movement. The control of the center of view of the medical image may be performed by a movement of the medical imaging device and/or by moving the center of view of the medical image without moving the medical imaging device but the medical image. Thus, even if the head of the operator is moved to select one of the command fields, the predetermined center of view of the medical image may be viewed by the operator. Furthermore, as some functions may be controlled by the eye movement without selecting command fields of the command menu, the number of command fields may be reduced.

In some embodiments, the head-mounted display is configured to display a visual indicator in the display representative of the tracked movement and/or to highlight a selected one of the command fields and/or the confirmation field.

A visual indicator may be a cursor-like item displayed in the display of the head-mounted display to provide a visual control. Alternatively or in addition, a command field and/or confirmation field selected may be highlighted to provide feedback to the operator upon such selection. The highlighting of the selected command field and/or confirmation field may be visually, acoustically and/or tactilely. Such feedback enhances the control abilities of the operator and therefore mitigates the risk of executing unintended commands.

According to the disclosure, the medical imaging device may be a surgical microscope, preferably a robotic microscope.

The use of the head-mounted display system for controlling a surgical microscope allows the operator to perform a surgery without taking the eyes and hands off the operating field. This is particularly advantageous in view of surgeries while using a surgical microscope as changes of the position of the hands of the surgeon and thereby possible changes of the position of the surgical instrument which are not caused by the surgery itself should be avoided. Additionally, a surgical procedure may be executed and visually controlled while controlling the microscope at the same time, e.g. to change the viewing angle or magnification. Further, the risk of contaminations is reduced.

Alternatively, the medical imaging device may be an endoscope.

The use of the head-mounted display system for controlling an endoscope also allows the operator to perform a surgery without taking the eyes and hands off the operating field similar to the use of the head-mounted display for controlling a microscope. In view of advantages regarding the respective control of a microscope, the hands of the surgeon, if no robotic guidance is used, have to hold the surgical instruments in the operating field which is comparably small and deep in most endoscopic surgeries. Accordingly, removing the hands to control the endoscope may cause difficulties in avoiding further injuries due to sharp surgical instruments and in replacing the instruments appropriately. Even if only one hand of the surgeon is used to handle a surgical instrument, the hand may be required to operate the endoscope. In such event, functionalities of the endoscope which are not incorporated in the handle of the endoscope or in near distance are not controllable by the surgeon's hand without releasing the surgical instrument or the endoscope. Although the endoscope or a surgical instrument may be supported or guided otherwise, e.g. by a surgical robot, the hands of the surgeon may be bound by other instruments or control devices.

In a further aspect, the disclosure is directed to a method for controlling a medical imaging device, comprising a head-mounted display system as described above, comprising the steps of:
a) displaying the command menu,
b) tracking the movement representative of the operator's eye and/or head movement,
c) selecting one of the command fields of the command menu by tracked movement of the operator's eye and/or head movement, wherein, if only a first set of commands is displayed, one of the distinct first command fields is selected when the direction and amount of the respective movement corresponds to a position of the respective distinct first command field or, if a first set and a second set of commands are displayed, one of the distinct second command fields is selected when the direction and amount of the respective movement corresponds to a position of the respective distinct second command field and one of the distinct first command fields (123a) is selected when the direction and amount of the respective movement corresponds to a position of the respective distinct first command field while no further movement exceeding a predetermined amount in a direction to one of the distinct second command fields is tracked, and
d) controlling the medical imaging device in accordance with a selected one of the command fields.

The direction and amount of movement may be tracked as relative or absolute coordinates. The direction and amount of movement may also be represented by the comparison of spatial positions.

In the event of only the first set of commands displayed, the control of the medical imaging device may be executed in accordance with the distinct first command field selected first or last. The distinct first command field selected last may be defined as the distinct first command field selected last after a predetermined time has lapsed or after a confirmation has been received as, for example, described below.

Similarly, if a first set and a second set of commands are displayed, the control of the medical imaging device may be executed in accordance with the distinct first command field selected first or last if no further movement exceeding a predetermined amount in a direction to one of the distinct second command fields is tracked after a predetermined time has lapsed or after a confirmation has been received. The control of the medical imaging device may be executed in accordance with the distinct second command field selected first or last. As for the distinct first command field, the distinct second command field selected last may be defined as the distinct first command field selected last after a predetermined time has lapsed or after a confirmation has been received.

In some embodiments, the step of controlling the medical imaging device in accordance with one of the selected command fields of the command menu further comprises the confirmation of the selected command field by moving the operator's eye or head to the confirmation field, wherein the selection is confirmed when the direction and amount of the respective movement corresponds to a position of the respective confirmation field.

Accordingly, the control of the medical imaging device is not dependent on any time constraints that may be prone to an unintended command execution but the selected command has to be intentionally confirmed to be executed.

In a further aspect, the disclosure is directed to a computer program product comprising a program code stored on a machine-readable medium, and, when being executed on a data processing device, configured to cause the data processing device to execute the method as described above.

The computer program product may provide the same functionalities and advantages as described with respect to the head-mounted display system and method for controlling an imaging device.

BRIEF DESCRIPTION OF THE SEVERAL VIEWS OF THE DRAWINGS

Further advantages, aspects and details of the disclosure are subject to the claims, the following description of preferred embodiments applying the principles of the disclosure and drawings. In the figures, identical reference signs denote identical features and functions.

BRIEF DESCRIPTION OF THE DRAWINGS

Figure 1:
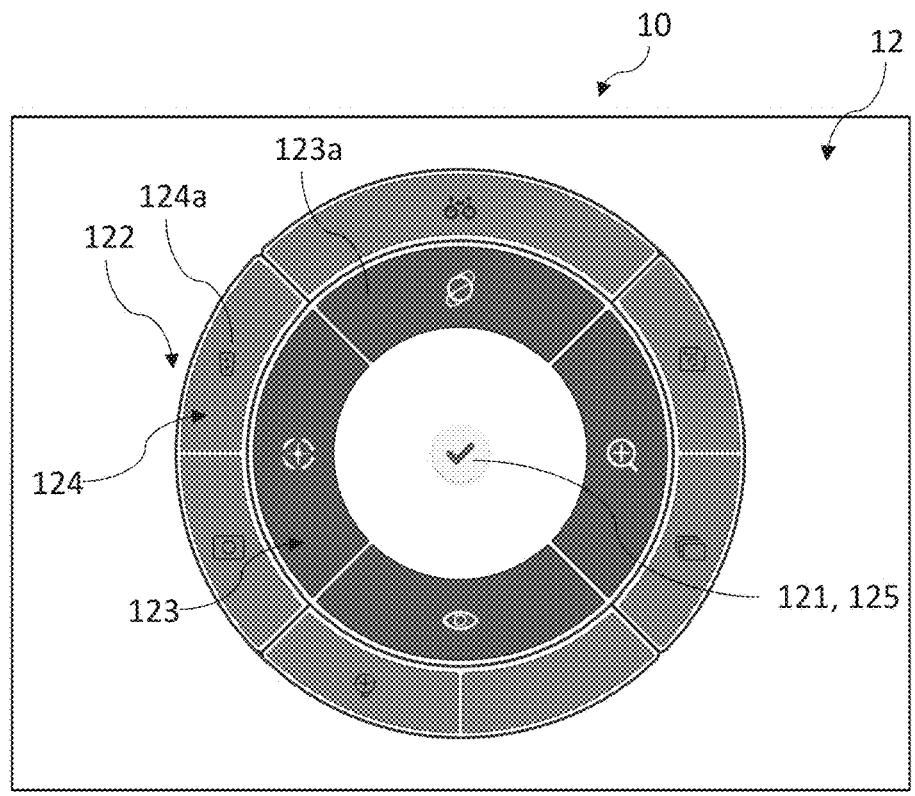
Figure 2:
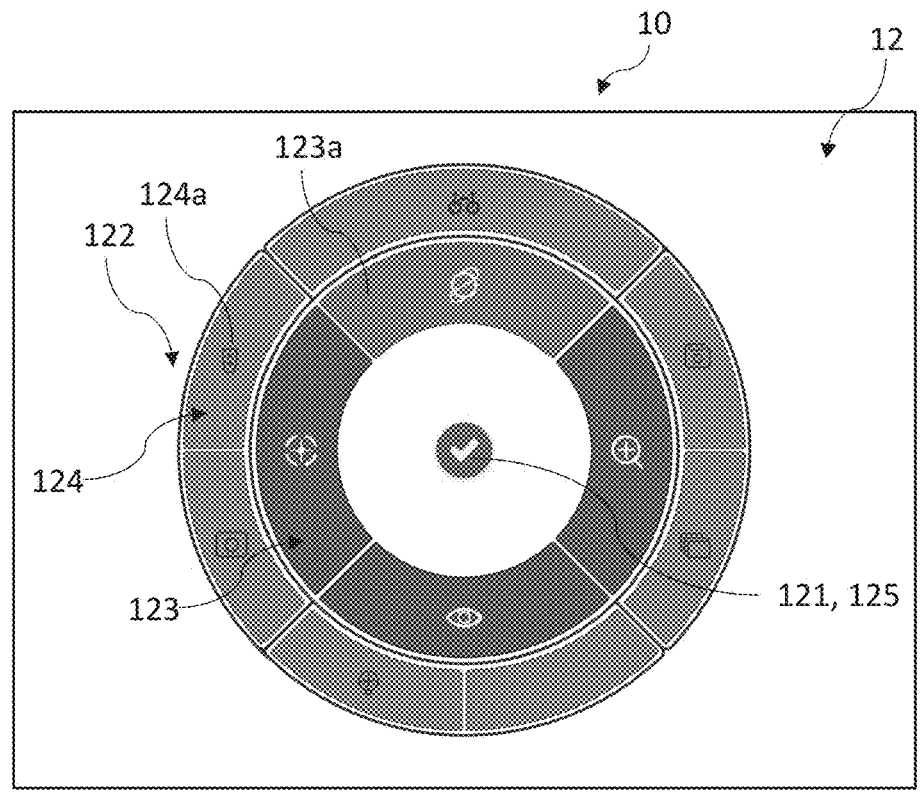
Figure 3:
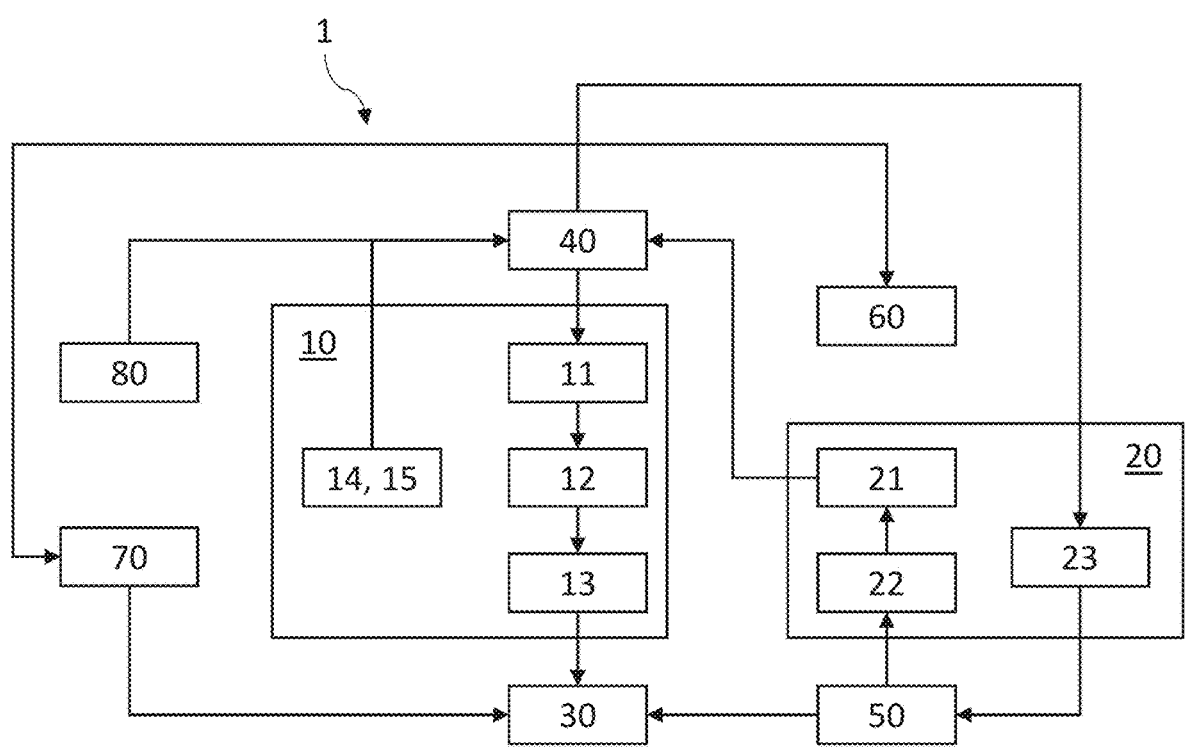

FIG. 1 is a schematic view of a head-mounted display showing the display and the command menu according to an exemplary embodiment;

FIG. 2 is a schematic view of the head-mounted display showing the display and the command menu according to FIG. 1 with a command field selected and confirmed; and FIG. 3 is a scheme of the disclosed head-mounted display system according to an exemplary embodiment.

DESCRIPTION OF SPECIFIC EMBODIMENTS OF THE INVENTION

FIG. 1 illustrates a schematic view of a head-mounted display 10 showing a display 12. The display 12 shows a command menu 122 comprising a first set of commands 123 and a second set of commands 124 arranged around a predetermined center of view 121. The first set of commands 123 is constituted by four distinct first command fields 123a arranged in equal first distances to the center of view 121. The first set of commands 123 may comprise distinct first command fields 123a to control the magnification, the viewing angle, the center of view or position of the focal plane. The first set of commands 123 is surrounded by a second set of commands 124. The second set of commands 124 comprises seven distinct second command fields 124a arranged in equal second distances to the center of view 121. The equal second distances are larger than the equal first distances. Here, the equal second distances are selected to arrange the distinct second command fields 124a adjacent to the distinct first command fields 123a in a direction extending radially from the center of view 121 to limit the required movement to be tracked to select different command fields 123a, 124a to a minimum. The second set of commands 124 may comprise distinct second command fields 124a to control the position of the display 12, to store images, adjust the light level, change the working distance, store and recall robot positions, or open add on related functions like view imaging data, switch to fluorescence mode, activate an infrared camera, open a surgical navigation or the like. In the exemplary embodiment, the first set of commands 123 is colored differently from the second set of commands 124 for identification reasons. Different colors, shades and/or transparency grades may be also used to indicate an activated or deactivated state of the first set of commands 123 and the second set of commands 124 and/or of distinct first command fields 123a and/or distinct second command fields 124a.

Further, FIG. 1 shows a confirmation field 125 positioned in the center of view 121. As the confirmation field 125 may cover relevant parts of the medical image in the center of view 121, the confirmation field 125 may only be displayed on demand, in particular, after activation of an input device 80 (FIG. 3) like a footswitch. Alternatively or in addition, the confirmation field 125 may only be displayed after a command field 123a, 124a has been selected. Even though the command menu 122 is not arranged in the center of view 121, the command menu 122 or at least parts thereof may also be only displayed on demand.

FIG. 2 shows a schematic view of the exemplary embodiment of FIG. 1 after a distinct first command field 123a, here, the upper distinct first command field 123a representing the control of the viewing angle, has been selected. The selection has been detected by tracking the operator's head movement by use of the tracking system 14 (FIG. 3), wherein a command field 123a, 124a is selected when the direction and amount of the respective movement corresponds to a position of a respective distinct first or second command field 123a, 124a. Accordingly, the tracked movement representative of the movement of the operator's head in terms of direction and amount corresponds to the upper distinct first command field 123a representing the control of the viewing angle. To indicate the selection, the upper distinct first command field 123a representing the control of the viewing angle is highlighted, i.e. the color of the distinct first command field 123a is changed. Highlighting may also be performed by other visual effects like changing a transparency grade or pattern, acoustical effects and/or tactile effects. With respect to visual effects, a selected command field 123a, 124a may not have to be highlighted over its whole area but may only provide a highlighted frame.

In the shown embodiment the selected distinct first command field 123a has to be confirmed before the control device 40 (FIG. 3) controls the medical imaging device 20 (FIG. 3) to execute the selected command. The selected distinct first command field 123a is confirmed if the tracked movement representative of the operator's head movement corresponds to the position of the confirmation field 125. The received confirmation is indicated by highlighting the confirmation field 125.

The confirmation field is displayed in the center of view 121. Accordingly, the selected command is executed after the operator's view can be assumed as directed on the center of view 121 as the relevant view on the operating field. Further, the center of view 121 may be assumed as the preferred posture of the operator to proceed.

FIG. 3 shows a scheme of the disclosed head-mounted display system 1 according to an exemplary embodiment applicable to the exemplary embodiment of the head-mounted display 10 illustrated in FIG. 1 and FIG. 2, respectively. The head-mounted display system 1 comprises the head mounted-display 10, a medical imaging device 20 to provide a medical image of a scene 50, a robot 60 to move the medical imaging device 20, a user interface 70 and an input device 80.

The medical imaging device 20 comprises a camera sensor 21 for capturing a medical image of a scene 50 via a lens 22 and a light 23 to illuminate the scene 50. The captured medical image is transmitted to the control device 40 to be forwarded to the head-mounted display 10. The head-mounted display 10 comprises a display driver 11 to receive the medical image and to transmit the medical image to the display 12 to be shown to the operator 30 via an eyepiece or two eyepieces 13. The user interface 70 may be an external screen controlled by the control device 40 to provide the operator 30 with different information and/or control abilities independent from the control of the medical imaging device 20 by the command menu 122 displayed on the display 12 of the head-mounted display 10.

To control the medical imaging device 20 based on a tracked movement representative of the operator's head and/or eye movement, a tracking system 14 is incorporated in the head-mounted display 10. For explanatory reasons, the description of the embodiment shown in FIG. 3 is directed to a tracked movement of the head of the operator 30. However, the same principles apply to tracked movement of the operator's eye or a combination of a tracked head and eye movement of the operator 30.

The tracking system 14 may be incorporated in the head-mounted display 10 as 3D acceleration sensor or inertial measurement unit and provides the control device 40 with information about the direction and amount of the tracked movement. The tracked movement representative of the movement of the operator's head may be provided continuously or on demand. A demand may be expressed by activating the input device 80 to allow an operator to control the medical imaging device 20 based on such tracked movement. Furthermore, upon activation of the input device 80, e.g. a footswitch, the control device 40 causes the head-mounted display 10 to display the command menu 122 on the display 12. The command to be executed may be selected and confirmed as described with reference to FIGS. 1 and 2. However, other options for selecting or selecting and confirming a command according to the disclosure are also applicable.

To mitigate the risk of an unintended selection and execution of a command, the control device 40 may be configured to only display the command menu 122 and therefore allowing the selection of a command as long as a continuous activation action is applied to the input device 80. Furthermore, the head-mounted display 10 of the exemplary embodiment in FIG. 3 comprises a monitoring device 15 configured to monitor the position of the display 12 and to release the selection of one of the command fields 123a, 124a and/or to display the command menu 122 only in positions of the display 12 representing a use of the display 12 by the operator 30. In the exemplary embodiment in FIG. 3, the monitoring device 15 is implemented as contact switch which is closed when the display 12 is flipped-down in an operating state. However, the monitoring device may also be incorporated in the tracking system 14.

Although the control device 40 in FIG. 3 shows only a connection to the robot 60 to move the medical image device 20 and a connection to the light 23 of the medical imaging device 20 to control the brightness of the light 23, the control device 40 may be configured to control more functions to affect the medical image displayed in the display 12 of the head-mounted display 10. The number of connections is limited for illustrative clarity reasons only.

It is to be noted that the given examples are specific embodiments and not intended to restrict the scope of protection given in the claims. In particular, single features of one embodiment may be combined with another embodiment. As an example, the first set of commands 123 comprises four distinct first command fields 123a in the embodiment shown in FIG. 1 or FIG. 2, respectively. Even though the four distinct first command fields 123a may represent main tracking movements that may be easy to implement and being controlled, the first set of commands 123 may also comprise more or less distinct first command fields 123a. The same applies to the number of distinct second command fields 124a provided by the second set of commands 124. Further, the exemplary embodiment shown in FIG. 1 or FIG. 2, respectively, displays the first set of commands 123 and the second set of commands 124 simultaneously. However, the first set of commands 123 and the second set of commands 124 may also be displayed independently, e.g. on demand or according to different operating states. Further, even though the confirmation field 125 may be preferably positioned in the center of view 121, the confirmation field may be positioned near the center of view 121 as long as it can be assumed that the operator may be able to view the center of view 121 from such position.

LIST OF REFERENCE SIGNS 1 head-mounted display system
10 head-mounted display
11 display driver
12 display
13 eyepiece
14 tracking system
15 monitoring device
20 medical imaging system
21 camera sensor
22 lens
23 light
30 operator
40 control device
50 scene
60 robot
70 user interface
80 input device
121 center of view
122 command menu
123 first set of commands
123a first command field
124 second set of commands
124a second command field
125 confirmation field

What is claimed is:

1. Head-mounted display system (1) for controlling an endoscope or a surgical microscope as a medical imaging device (20), comprising:

a head-mounted display (10) to be worn by an operator, comprising a display (12) configured to display a medical image with a predetermined center of view (121) and a command menu (122) providing at least a first set of commands (123) as distinct first command fields, a tracking system (14) to track a movement representative of the operator's eye (30) and/or head movement, wherein a command of the at least first set of commands (122a) of the command menu (122) is selectable based on the tracked eye and/or head movement, and a control device (40) configured to receive a selected command and to control the medical imaging device (20) accordingly, wherein the distinct first command fields (123a) of said the at least first set of commands (123) of the commend menu (122) displayed on the display (12) of the head-mounted display (10) are arranged in substantially equal first distances from the predetermined center of view (121) of the medical image; and wherein the command menu (122) further comprises a confirmation field (125) arranged in the predetermined center of view (121) of the medical image to confirm the selected command field (123a, 124a);

wherein the confirmation field (125) is only displayed after a detection of at least one of:

an activation of an input device (80), and a selection of the command field (123a, 124a) by tracking at least one of a head movement and an eye movement of the operator by use of the tracking system.

2. The head-mounted display system (1) according to claim 1, wherein the command menu (122) provides a second set of commands (124) as distinct second command fields (124a) displayed on the display (12) of the head-mounted display (10) and arranged second distances from the predetermined center of view (121) of the medical image, wherein the second distances of the distinct second command fields (124a) are larger than the first distances of the distinct first command fields (123a).

3. The head-mounted display system (1) according to claim 2, wherein the control device (40) is configured to deactivate the distinct first command fields (123a) when the tracking system (14) indicates that the tracked movement has passed one of the distinct first command fields (123a) in a direction away from the predetermined center of view (121) of the medical image to one of the distinct second command fields (124a).

4. The head-mounted display system (1) according to claim 2, wherein the control device (40) is configured to assign commands to the first set of commands (123) and the second set of commands (124) based on a frequency and/or probability of use.

5. The head-mounted display system (1) according to claim 4, wherein the control device (40) is configured to adapt the assignment of commands to the first set of commands (123) and the second set of commands (124) based on a changed frequency and/or probability of use.

6. The head mounted display system (1) according to claim 2, wherein the second command fields (124a) are arranged in substantially equal second distances from the predetermined center of view (121).

7. The head-mounted display system (1) according to claim 1, wherein the input device (80) is activated as a prerequisite for the selection of one of the command fields (123a, 124a) and/or for displaying the command menu (122).

8. The head-mounted display system (1) according to claim 7, wherein the input device (80) is configured to be only activated as long as a continuous activation action is applied.

9. The head-mounted display system (1) according to claim 7, wherein the input device (80) is a footswitch.

10. The head-mounted display system (1) according to claim 1, wherein the head-mounted display system (1) further comprises a monitoring device (15) configured to monitor the position of the display (12) and to release the selection of one of the command fields (123a, 124a) and/or to display the command menu (122) only in positions of the display (12) representing a use of the display (12) by the operator (30).

11. The head-mounted display system (1) according to claim 1, wherein the head-mounted display system (1) further provides different operating states and is configured to release the selection of one of the command fields (123a, 124a) and/or display the command menu (122) only in predetermined operating states.

12. The head mounted display system (1) according to claim 1, wherein the tracking system (14) is configured to track the movement representative of the eye movement to control the center of view (121) of the medical image on the display and to track the movement representative of the head movement to select one of the command fields (123a, 124a).

13. The head mounted display system (1) according to claim 1, wherein the head-mounted display (10) is configured to display a visual indicator in the display (12) representative of the tracked movement and/or to highlight a selected one of the command fields (123a, 124a) and/or the confirmation field (125).

14. The head mounted display system (1) according to claim 1, wherein the medical imaging device (20) is a surgical microscope.

15. The head mounted display system (1) according to claim 14, wherein the surgical microscope is a robotic microscope.

16. The head mounted display system (1) according to claim 14, wherein the input device is a footswitch.

17. The head mounted display system (1) according to claim 1, wherein the medical imaging device (20) is an endoscope.

18. Method for controlling a medical imaging device (20), comprising a head-mounted display system (1) according to claim 1, comprising the steps of:

a) displaying the command menu (122), b) tracking the movement representative of the operator's eye (30) and/or head movement, c) selecting one of the command fields (123a, 124a) of the command menu (122) by tracked movement of the operator's eye (30) and/or head movement, wherein, if only a first set of commands (123) is displayed, one of the distinct first command fields (123a) is selected when the direction and amount of the respective movement corresponds to a position of the respective distinct first command field (123a) or, if a first set and a second set of commands (124) are displayed, one of the distinct second command fields (124a) is selected when the direction and amount of the respective movement corresponds to a position of the respective distinct second command field (124a) and one of the distinct first command fields (123a) is selected when the direction and amount of the respective movement corresponds to a position of the respective distinct first command field (123a) while no further movement exceeding a predetermined amount in a direction to one of the distinct second command fields (124a) is tracked, and d) controlling the medical imaging device (20) in accordance with a selected one of the command fields (123a, 124a).

19. The method according to claim 18, wherein the step of controlling the medical imaging device in accordance with one of the selected command fields (123a, 124a) of the command menu (122) further comprises the confirmation of the selected command field (123a, 124a) by moving the operator's eye (30) or head to the confirmation field (125), wherein the selection is confirmed when the direction and amount of the respective movement corresponds to a position of the respective confirmation field (125).

20. A non-transitory tangible media product comprising a program code stored on a non-transitory tangible machine-readable medium, and, when being executed on a data processing device, configured to cause the data processing device to execute the method according to claim 18.

21. The head mounted display system (1) according to claim 14, wherein the selection of the command field (123*a*, 124*a*) is by tracking the at least one of a head movement and an eye movement of the operator by use of the tracking system.

* * * * *

UNITED STATES PATENT AND TRADEMARK OFFICE
CERTIFICATE OF CORRECTION

| | | |
|---|---|---|
| PATENT NO. | : 11,614,622 B2 | Page 1 of 1 |
| APPLICATION NO. | : 17/145429 | |
| DATED | : March 28, 2023 | |
| INVENTOR(S) | : Michael Mair et al. | |

It is certified that error appears in the above-identified patent and that said Letters Patent is hereby corrected as shown below:

On the Title Page

Item [30], "20151040" should be changed to --20151040.1--

Signed and Sealed this
Twenty-first Day of May, 2024

*Katherine Kelly Vidal*

Katherine Kelly Vidal
*Director of the United States Patent and Trademark Office*